United States Patent [19]

Schnur

[11] Patent Number: 5,851,968

[45] Date of Patent: Dec. 22, 1998

[54] INCREASING THE ELECTRICAL RESISTIVITY OF ESTER LUBRICANTS, ESPECIALLY FOR USE WITH HYDROFLUOROCARBON REFRIGERANTS

[75] Inventor: Nicholas E. Schnur, Cincinnati, Ohio

[73] Assignee: Henkel Corporation, Plymouth Meeting, Pa.

[21] Appl. No.: 552,444

[22] Filed: Nov. 3, 1995

Related U.S. Application Data

[63] Continuation of Ser. No. 247,790, May 23, 1994, abandoned.

[51] Int. Cl.$^6$ .............................. C09K 5/04; H01B 3/20; C10M 105/38

[52] U.S. Cl. .......................... 508/485; 508/492; 252/68; 252/579

[58] Field of Search .............................. 252/68, 500, 579; 508/485, 492, 493, 494, 495, 496, 497, 498; 174/8, 137 R

[56] References Cited

U.S. PATENT DOCUMENTS

| | | |
|---|---|---|
| Re. 19,265 | 8/1934 | Midgley et al. . |
| 2,040,902 | 5/1936 | Zellhoefer . |
| 2,084,950 | 6/1937 | Downing et al. . |
| 2,187,388 | 1/1940 | Williams et al. . |
| 2,520,612 | 8/1950 | Roberts et al. . |
| 2,548,493 | 4/1951 | Robey . |
| 2,575,195 | 11/1951 | Smith . |
| 2,575,196 | 11/1951 | Smith . |
| 2,628,974 | 2/1953 | Sanderson . |
| 2,717,242 | 9/1955 | Foehr . |
| 2,807,155 | 9/1957 | Williamitis . |
| 2,852,470 | 9/1958 | Henne et al. . |
| 2,926,139 | 2/1960 | Mott et al. . |
| 2,958,706 | 11/1960 | Hurwitz et al. . |
| 2,961,406 | 11/1960 | McNeil . |
| 2,962,419 | 11/1960 | Minich . |
| 3,135,785 | 6/1964 | Fritz . |
| 3,189,629 | 6/1965 | Huttenlocher et al. . |
| 3,194,791 | 7/1965 | Wilson et al. . |
| 3,202,701 | 8/1965 | Young et al. . |
| 3,282,971 | 11/1966 | Metro et al. . |
| 3,309,318 | 3/1967 | Aylesworth et al. . |
| 3,328,283 | 6/1967 | Godar . |
| 3,328,285 | 6/1967 | Godar . |
| 3,341,574 | 9/1967 | Taylor et al. . |
| 3,441,600 | 4/1969 | Chao et al. . |
| 3,523,084 | 8/1970 | Chao et al. . |
| 3,560,387 | 2/1971 | Schritt . |
| 3,562,300 | 2/1971 | Chao et al. . |
| 3,564,044 | 2/1971 | Chao et al. . |
| 3,694,382 | 9/1972 | Kleiman et al. . |
| 3,773,668 | 11/1973 | Denis et al. . |
| 3,778,454 | 12/1973 | Kleiman et al. . |
| 3,850,824 | 11/1974 | Nebzydoski et al. . |
| 3,855,508 | 12/1974 | Ross et al. ............... 252/579 |
| 3,878,112 | 4/1975 | Luck et al. . |
| 3,894,959 | 7/1975 | Gardiner et al. ............ 252/579 |
| 3,939,201 | 2/1976 | Bacskai . |
| 4,045,376 | 8/1977 | Rubin et al. . |
| 4,049,563 | 9/1977 | Burrous . |
| 4,053,491 | 10/1977 | Koch et al. . |
| 4,113,642 | 9/1978 | Koch et al. . |
| 4,144,183 | 3/1979 | Koch et al. . |
| 4,155,861 | 5/1979 | Schmitt et al. . |
| 4,159,255 | 6/1979 | Gainer et al. . |
| 4,175,045 | 11/1979 | Timony . |
| 4,178,261 | 12/1979 | Dhein et al. . |
| 4,199,461 | 4/1980 | Olund . |
| 4,212,816 | 7/1980 | Hentschel et al. . |
| 4,234,497 | 11/1980 | Honig . |
| 4,243,540 | 1/1981 | Mancini et al. . |
| 4,248,726 | 2/1981 | Uchinuma et al. . |
| 4,263,159 | 4/1981 | Berens et al. . |
| 4,267,064 | 5/1981 | Sasaki et al. . |

(List continued on next page.)

FOREIGN PATENT DOCUMENTS

| | | |
|---|---|---|
| 252876 | 12/1960 | Australia . |
| 0089709A1 | 9/1983 | European Pat. Off. . |
| 195110 | 9/1986 | European Pat. Off. . |
| 0227477A2 | 7/1987 | European Pat. Off. . |
| 272575 | 6/1988 | European Pat. Off. . |
| 315069 | 5/1989 | European Pat. Off. . |
| 336171 | 10/1989 | European Pat. Off. . |
| 406479 | 10/1989 | European Pat. Off. . |
| 479338 | 10/1989 | European Pat. Off. . |
| 480479 | 10/1989 | European Pat. Off. . |
| 0359071A1 | 3/1990 | European Pat. Off. . |
| 0377122A1 | 7/1990 | European Pat. Off. . |

OTHER PUBLICATIONS

Alcoa Industrial Chemicals Division SEP 920, Chemicals Product Data—"Granular Activated Alumina", Feb. 1992.

Neopentyl Polyol Ester Lubricants–Bulk Property Optimization; Niedzielski, Edmund; Ind. Eng. Chem., Prod. Res. Dev., vol. 15 No. 1, 1976 (Month Unknown).

Lubricants and Related Products, pp. 122–125; Klamann, Dieter; 1984 (Month Unknown).

Synthetic Ester Lubricants; Barnes, R.S. et al.; Lubrication Engineering; August 1957.

New Type Lube Oil for HFC–134a Compressor System; Takeno, T. et al.; 1992 (Month Unknown).

Synthetic Lubricants (Ch. 10, Neopentyl Polyol Esters); Smith, Thomas; 1962; Midland, Michigan (Month Unknown).

Complex Esters of 2,2–Dimethylhydracrylic Acid; Lederle, Henry F.; New Haven, CT; Mar. 1969.

(List continued on next page.)

*Primary Examiner*—Alan Diamond
*Attorney, Agent, or Firm*—Wayne C. Jaeschke; Norvell E. Wisdom, Jr.; John S. Child, Jr.

[57] ABSTRACT

The electrical resistivity of hindered polyol ester lubricants can be raised to very high levels by treating the lubricants with activated alumina, preferably after the acid values of the lubricants treated have already been reduced to low levels by conventional refining with alkali or other acid scavengers.

29 Claims, No Drawings

5,851,968
Page 2

U.S. PATENT DOCUMENTS

| | | |
|---|---|---|
| 4,292,187 | 9/1981 | Hentschel et al. . |
| 4,302,343 | 11/1981 | Carswell et al. . |
| 4,304,678 | 12/1981 | Schick et al. . |
| 4,320,018 | 3/1982 | Yaffe . |
| 4,324,676 | 4/1982 | Gilbert . |
| 4,359,394 | 11/1982 | Gainer et al. . |
| 4,371,577 | 2/1983 | Sato et al. . |
| 4,428,854 | 1/1984 | Enjo et al. . |
| 4,431,557 | 2/1984 | Shimizu et al. . |
| 4,440,660 | 4/1984 | van Rijs et al. . |
| 4,454,052 | 6/1984 | Shoji et al. . |
| 4,455,247 | 6/1984 | Nakayama et al. . |
| 4,487,874 | 12/1984 | Lindner . |
| 4,530,772 | 7/1985 | Timony . |
| 4,557,850 | 12/1985 | Ando et al. . |
| 4,559,154 | 12/1985 | Powell . |
| 4,626,959 | 12/1986 | Shedigian et al. ............ 252/579 |
| 4,719,025 | 1/1988 | Akiyama et al. . |
| 4,751,012 | 6/1988 | Ward et al. . |
| 4,755,316 | 7/1988 | Magid et al. . |
| 4,758,366 | 7/1988 | Parekh . |
| 4,780,229 | 10/1988 | Mullin . |
| 4,812,262 | 3/1989 | Shinzawa et al. ............ 252/579 |
| 4,826,633 | 5/1989 | Carr et al. . |
| 4,851,144 | 7/1989 | McGraw et al. . |
| 4,900,463 | 2/1990 | Thomas et al. . |
| 4,927,554 | 5/1990 | Jolley et al. . |
| 4,938,887 | 7/1990 | Grava et al. . |
| 4,941,986 | 7/1990 | Jolly . |
| 4,944,890 | 7/1990 | Deeb et al. . |
| 4,948,525 | 8/1990 | Sasaki et al. . |
| 4,959,169 | 9/1990 | McGraw et al. . |
| 4,963,282 | 10/1990 | Jolley et al. . |
| 4,992,188 | 2/1991 | Jolley . |
| 5,008,028 | 4/1991 | Jolley et al. . |
| 5,021,179 | 6/1991 | Zehler et al. . |
| 5,021,180 | 6/1991 | McGraw . |
| 5,023,007 | 6/1991 | Grava et al. . |
| 5,032,305 | 7/1991 | Kamakura et al. . |
| 5,032,306 | 7/1991 | Cripps . |
| 5,053,155 | 10/1991 | Mahler . |
| 5,057,247 | 10/1991 | Schmid et al. . |
| 5,061,550 | 10/1991 | Shimizu et al. . |
| 5,080,816 | 1/1992 | Sakamoto et al. . |
| 5,096,606 | 3/1992 | Hagihara et al. ............ 252/68 |
| 5,137,650 | 8/1992 | Kaneko . |
| 5,158,698 | 10/1992 | Jolley et al. . |
| 5,185,092 | 2/1993 | Fukuda et al. ............ 508/440 |
| 5,202,044 | 4/1993 | Hagihara et al. . |
| 5,211,884 | 5/1993 | Bunemann et al. . |
| 5,262,076 | 11/1993 | Ishida et al. . |
| 5,273,410 | 12/1993 | Kitaichi et al. . |
| 5,290,465 | 3/1994 | Sabahi . |
| 5,310,492 | 5/1994 | Seiki et al. . |
| 5,354,486 | 10/1994 | Evans . |
| 5,391,313 | 2/1995 | Antika et al. . |
| 378176 | 7/1990 | European Pat. Off. . |
| 379175 | 7/1990 | European Pat. Off. . |
| 0384724A1 | 8/1990 | European Pat. Off. . |
| 430657 | 11/1990 | European Pat. Off. . |
| 435253 | 12/1990 | European Pat. Off. . |
| 445610 | 2/1991 | European Pat. Off. . |
| 445611 | 2/1991 | European Pat. Off. . |
| 415778 | 3/1991 | European Pat. Off. . |
| 448402 | 3/1991 | European Pat. Off. . |
| 458584 | 5/1991 | European Pat. Off. . |
| 0440069A1 | 8/1991 | European Pat. Off. . |
| 0449406A1 | 10/1991 | European Pat. Off. . |
| 0452509A1 | 10/1991 | European Pat. Off. . |
| 0458584A1 | 11/1991 | European Pat. Off. . |
| 0461262B1 | 12/1991 | European Pat. Off. . |
| 522167 | 12/1991 | European Pat. Off. . |
| 468729 | 1/1992 | European Pat. Off. . |
| 479338 | 4/1992 | European Pat. Off. . |
| 480479 | 4/1992 | European Pat. Off. . |
| 498152 | 8/1992 | European Pat. Off. . |
| 0536814A1 | 4/1993 | European Pat. Off. . |
| 2154524 | 5/1973 | France . |
| 2302290 | 10/1976 | France . |
| 133966 | 1/1979 | Germany . |
| 2943446 | 5/1980 | Germany . |
| 2943446A1 | 5/1980 | Germany . |
| 1768765 | 10/1980 | Germany . |
| 4105956 | 8/1992 | Germany . |
| 53-136170 | 11/1978 | Japan . |
| 53-143609 | 12/1978 | Japan . |
| 54-040260 | 3/1979 | Japan . |
| 55-145638 | 11/1980 | Japan . |
| 55-155093 | 12/1980 | Japan . |
| 56-36570 | 4/1981 | Japan . |
| 56-131548 | 10/1981 | Japan . |
| 57-078475 | 5/1982 | Japan . |
| 58-15592 | 1/1983 | Japan . |
| 59-027979 | 2/1984 | Japan . |
| 59-029625 | 2/1984 | Japan . |
| 59-21632 | 2/1984 | Japan . |
| 61-62596 | 3/1986 | Japan . |
| 62-290795 | 12/1987 | Japan . |
| 485396 | 3/1992 | Japan . |
| 96079 | 4/1962 | Romania . |
| 1057526 | 11/1983 | U.S.S.R. . |
| 644597 | 10/1950 | United Kingdom . |
| 662650 | 12/1951 | United Kingdom . |
| 760490 | 10/1956 | United Kingdom . |
| 889067 | 2/1962 | United Kingdom . |
| 892943 | 4/1962 | United Kingdom . |
| 894639 | 4/1962 | United Kingdom . |
| 1028402 | 5/1966 | United Kingdom . |
| 1460665 | 2/1974 | United Kingdom . |
| 2216541 | 10/1989 | United Kingdom . |
| WO88/08023 | 10/1988 | WIPO . |
| 9005831 | 5/1990 | WIPO . |
| WO90/12849 | 11/1990 | WIPO . |
| WO91/05831 | 5/1991 | WIPO . |
| WO92/01030 | 1/1992 | WIPO . |
| WO93/01249 | 1/1993 | WIPO . |
| WO93/11210 | 6/1993 | WIPO . |

OTHER PUBLICATIONS

Grant & Hackh's Chemical Dictionary 5th Edition; 1987, pp. 11 and 284 (Month Unknown).

Hawley's Condensed Chemical Dictionary 11th Edition; 1987, p. 214 (Month Unknown).

Das FCKW–Problem Fur die Kaltetechnik; Hesse, Ullrich et al.; 1988 (German) (Month Unknown).

Abstract 17463, From du Pont de Nemours & Co., (Date Unknown).

Chemical Abstract, vol. 102 (1985) No. 2 p. 166, #9492µ, (Month Unknown).

H.H. Kruse and M. Schroeder, "Fundamentals of Lubrication in Refrigerating Systems and Heat Pumps", ASHRAE Transactions, vol. 90, Part 2B, KC–84–14, p. 763, Kansas City, Missouri, 1984. (Month Unknown).

WPAT Abstract #90–084916/12 for EP 359071, Mar. 1990.

WPAT Abstract #87–102678/15 for EP 218207, Apr. 1987.

WPAT Abstract #68–38171Q/00 for CA 819715, (Date Unknown).

WPAT Abstract #70–81056R/44 for CA 854728 (Date Unknown).

WPAT Abstract #70–84646R/46 for GB 1028402 (Date Unknown).
WPAT Abstract #91–281860/39 for CA 2022832 Jul. 1991.
WPAT Abstract #92–286118/35 for EP 499994, Aug. 1992.
WPAT Abstract #91–231815/32 for EP 440069 Aug. 1991.
Predicting Behavior of Oils in Refrigeration Systems:, Bosworth, C.M., Refrigerating Engineering, Jun. 1952.
Synthetic Lubricants and Their Refrigeration applications, Short, Glenn D. Presented at the 44th Annual Meeting of the Society of Tribologists and Lubrication Engineers, Atlanta, Georgia, May 1–4, 1989, pp. 1–9.
Diester Compressor Oils in Refrigeration, Fluid & Lubrication Ideas, Fall, 1979 pp. 25, 26 (Month Unknown).
CA 110:215912z Synthetic Oil For Use With R–22 and R–502 Cooling Agents Texhnol. Topl. Mosel (1989) (Month Unknown).
CA 104:227382r Synthetic Lubricants for Regrigeration Systems, Seto, Kazuki (Matsumora Oil Co. Ltd., Japan) REITO 1985 69(694) 802–9 (Month Unknown).
Evaluation of Lubricants for Refrigeration and Air–Condition Compressors, Spauschus, Hans O. Cite Ashrae Transactions 90 (Pt. 2B): 784–798 (1984) (Month Unknown).
Three–page document with not relevant information redacted, bearing date more than one year before the filing date and entitled "Report of Visit", and bearing headings including Company, Contact and Date on the first page of document. (Date Unknown).
Three–page document with not relevant information redacted, bearing date more than one year before filing date and identifying "Freon 502 Compatibility Testing" as the subject of document. (Date Unknown).
Two–page document with not relevant information redacted, bearing date more than one year before the filing date and relating to Requisition LS–253. Date Unknown).
One–page document with not relevant information redacted, bearing date more than one year before the filing date and identifying Freon Compatibility of Emgard Compressor Oils ad the "subject" of document. (Date Unknown).

Two–page letter with not relevant information redacted, bearing date more than one year before the filing date and referring to a request for the correct viscosity for compressors of a third party. (Date Unknown).
One–page table with not relevant information redacted and referencing compositions of ester lubricants. (Date Unknown).
Certificates of Analyses numbered 1–35. The Certificates of Analyses pertain to "E32" with non relevant material blanked out. The 35 Certificates of Analyses relate to activities and shipments of material more than one year prior to Jul. 12, 1990, the filing date of U.S. Ser. No. 551,969, which issued as U.S. Patent 5,021,179 to Zehler et al. Each Certificate of Analyses bears a date more than one year prior to Jul. 12, 1990. (Date Unknown).
A. Al'tman et al., "Synthetic Lubricant", Translation of Russian Patent No. 208868 (Application No. 1028071/23–4), Sep. 18, 1965.
K. Sandvordenker et al., "A Review of Synthetic Oils for Refrigeration Use", Ashrae Symposium Bulletin NA–72–5, Nassau, Bahamas (Date Unknown).
Chemical Abstract, vol. 96 71653H Nov. 1980.
K. Sandvordenker, "Materials Compatibility of R134S in Refrigerant Systems", CFCS: Time of Transition, American Society of Heating, Refrigerating and Air–Conditioning Engineers, Inc., pp. 211–216, Jan. 1989.
Mobil Chemical, "Ester Base Stock", Data Sheets for Mobil Esters P41 and P51 (Date Unknown).
JAPIO Abstract #01452793 for JP 59–164393, Sep. 1984.
JAPIO Abstract #00478758 for JP 54–130758, Nov. 1979.
JAPIO Abstract #01310032 for JP 59–021632, Feb. 1984.
JAPIO Abstract #01654522 for JP 60–133022, Jul. 1985.
Abstract for JP 56–133241 Oct. 1981.
JAPIO Abstract #02961493 for JP 1–259093, Oct. 1989.
JAPIO Abstract #02961495 for JP 1–259095, Oct. 1989.
Abstract for JP 56–131,548, Oct. 1981.
Abstract for JP 56–125,495, Oct. 1981.

INCREASING THE ELECTRICAL RESISTIVITY OF ESTER LUBRICANTS, ESPECIALLY FOR USE WITH HYDROFLUOROCARBON REFRIGERANTS

This application is a continuation of application Ser. No. 08/247,790 filed on May 23, 1994 now abandoned.

BACKGROUND OF THE INVENTION

1. Field of the Invention

This invention relates to processes for increasing the electrical resistivity of ester lubricants, particularly esters of hindered polyols, which are defined for this purpose as organic molecules containing at least five carbon atoms, at least 2 —OH groups, and no hydrogen atoms on any carbon atom directly attached to a carbon atom bearing an —OH group, more particularly such esters that are intended to be used to lubricate refrigerating compressors and similar machinery which will bring the lubricant esters into contact with, and thus form mixtures of them with, hydrofluorocarbon refrigerants. Substantially chlorine-free hydrofluorocarbon refrigerants (hereinafter often abbreviated as "HFC's") are scheduled by international treaty and the laws and regulations of most industrially advanced countries to replace the most common previously used chlorofluorocarbon refrigerant heat transfer fluids ("CFC's"), in order to reduce the threat to the earth's ozone layer from the chlorine content of the emissions from imperfectly sealed and/or discarded refrigerators.

2. Statement of Related Art and Object of the Invention

CFC's and the mineral oil lubricants normally used with them generally have high electrical resistivities. This resistivity was relied on to provide an important part of the electrical insulation needed in many existing compressor designs. Commercial HFC's themselves are more polar than and have lower electrical resistance than commercial CFC's, and commercial examples of the ester type lubricants that are often needed for adequate miscibility with HFC's have often had considerably lower electrical resistance than commercial mineral oil lubricants. There is therefore a demand for lubricants with higher electrical resistivities that also are well adapted for use with HFC's.

Esters of hindered polyols have already been recognized in the art as high quality lubricant basestocks for almost any type of refrigeration machinery employing a fluorocarbon refrigerant, particularly one free from chlorine. However, these esters as practically made have often not had adequate electrical resistivity for the uses most demanding of this property. Providing such esters with higher electrical resistivity is a major object of this invention.

DESCRIPTION OF THE INVENTION

Except in the claims and the operating examples, or where otherwise expressly indicated, all-numerical quantities in this description indicating amounts of material or conditions of reaction and/or use are to be understood as modified by the term "about" in defining the broadest scope of the invention. Practice of the invention within the boundaries corresponding to the numerical quantities stated is usually preferable, however. Also, unless explicitly stated to the contrary, the description of more than one chemical compound or class of compounds as suitable or preferred for a particular purpose in connection with the invention shall be understood as implying that mixtures of any two or more of the entities so described individually as suitable or preferred are equally as suitable or preferred as the individual entities, and all descriptions of mixtures in terms of ratios, percentage, or parts shall be understood as ratios, percentages, or parts by weight or mass.

SUMMARY OF THE INVENTION

It has now been found that treatment with activated alumina is surprisingly effective in increasing the electrical resistivity of lubricant esters as commonly made commercially in the past, even when the esters have already been extensively refined to reduce their acid values. This treatment is particularly effective when applied to esters of the types described in copending U.S. patent application Ser. Nos. 08/027,628, 08/027,629, 08/028,856, 08/029,194, 08/029,196, and 08/029,204, all filed Mar. 10, 1993, and in U.S. Pat. No. 5,021,179 of Jun. 4, 1991 to Zehler et al., the complete specifications of all of which, except to any extent contrary to any explicit statement herein, are hereby incorporated herein by reference.

DESCRIPTION OF PREFERRED EMBODIMENTS

A process according to this invention at a minimum includes a step of contacting a liquid lubricant ester containing composition, also containing some impurities of unknown chemical character that are present in the starting materials and/or produced during the esterification reaction under practical conditions, with solid activated alumina, maintaining the contact for a selected period of time, and then separating the solids to produce a product liquid lubricant ester containing mixture with higher electrical resistivity. Preferably, contact between the solid activated alumina and the lubricant to be refined is assisted by mechanical agitation.

The temperature during contact between the lubricant and alumina preferably is, with increasing preference in the order given, at least 30°, 52°, 72°, 90°, 98°, 105°, 111°, 116°, or 119° C. and independently preferably is, with increasing preference in the order given, not more than 300°, 210°, 188°, 168°, 150°, 142°, 134°, 128°, 124°, or 121° C.

The time of contact between alumina and ester before separation preferably is, with increasing preference in the order given, not less that 1, 2, 4, 8, 16, 32, 40, 48, 52, or 56 minutes (hereinafter often abbreviated "min") and independently preferably is, with increasing preference in the order given, not more than 480, 360, 300, 280, 265, 255, 250, or 244 min.

The ratio, expressed as percentage, of the mass of activated alumina used to the mass of liquid treated preferably is, with increasing preference in the order given, not less than 0.01, 0.02, 0.04, 0.08, 0.16, 0.26, 0.35, 0.39, 0.43, 0.46, or 0.48% and independently not more than 10, 5, 2.5, 1.8, 1.3, 0.80, 0.67, 0.62, 0.58, 0.55, or 0.52%.

The average particle size of the activated alumina used in the process preferably is chosen to be sufficiently large to separate easily when desired, by some well established and economical process such as filtration or centrifugation, and sufficiently small and/or porous to have a high surface area, inasmuch as it is believed that adsorption may contribute significantly to the increases in electrical resistivity achieved by a process according to the invention. More particularly, the alumina used preferably is, with increasing preference in the order given, fine enough to pass through screens with standard mesh sizes of 24, 40, 50, 60, 80, or 100 mesh and independently preferably is, with increasing preference in the order given, not fine enough to pass through screens or cloths with standard mesh sizes of 1000, 600, 400, or 320.

Independently the specific surface area of the alumina used, measured by the conventional Brunauer-Emmett-Teller ("BET") nitrogen gas adsorption technique, is at least, with increasing preference in the order given, 100, 150, 200, 225, or 250 square meters per gram (hereinafter abbreviated as "$m^2/g$").

Under some conditions it is advantageous to reduce the pressure over the mixture of activated alumina and lubricant being treated according to the invention. When such a partial vacuum is desired, the pressure of gas over the mixture of alumina and esters being treated preferably is, with increasing preference in the order given, not more than 100, 50, 25, 15, 10, 8, 7, 6, or 5 torr during at least half of the total contact time.

The conditions above have been described for a single application of a process according to the invention. In practice, however, it has been found advantageous in many cases to repeat one or all of the steps of the process outlined above at least once, and sometimes more than once, as indicated in the working examples below. A somewhat less preferred, but nevertheless often useful, alternative to repeating all the steps outlined above is to use amounts of alumina nearer to the upper limits of the preferred values in a single step, rather than amounts nearer to the most preferred values. For example, instead of using 0.5% alumina three times, 1.5% alumina might be used in a single step.

The effectiveness of activated alumina in raising electrical resistivity is substantially reduced if the lubricant ester containing mixture being treated contains free acids of any sort. Therefore, the lubricant mixture to be treated according to the invention preferably is first treated if necessary by alkali refining as generally known in the art in order to reduce its acid value (hereinafter often abbreviated as "AV"). The AV of the lubricant mixture to be treated before beginning treatment according to the invention preferably is, with increasing preference in the order given, not greater than 0.10, 0.085, 0.065, 0.050, 0.040, 0.032, 0.028, 0.026, 0.024, 0.022, 0.020, 0.018, 0.016, 0.014, 0.012, or 0.010.

The effectiveness of the alumina can also be reduced by water present in the liquid being treated. Therefore, the liquid to be treated preferably is dried by partial vacuum and heat and/or by contact with desiccant before treatment according to this invention. One suitable method of drying is to maintain the ester mixture at 120° C. for about 2 hours under a partial vacuum, with a pressure of not more than 2 torr, or preferably not more than 0.2 torr. However, other drying methods known in the art may also be used.

The volume resistivity, measured according to ASTM method D 1169-80, of a lubricant product from a process according to this invention preferably is, with increasing preference in the order given, at least $1.0 \cdot 10^{14}$, $2.0 \cdot 10^{14}$, $4.0 \cdot 10^{14}$, $5.9 \cdot 10^{14}$, $6.8 \cdot 10^{14}$, $8.0 \cdot 10^{14}$, $9.0 \cdot 10^{14}$, or $10.0 \cdot 10^{14}$ ohm centimeters.

A process according to the invention is particularly advantageously applied to esters made by reacting hindered polyols, preferably neopentyl glycol ("NPG"), trimethylolpropane ("TMP"), or pentaerythritol ("PE"), with pentanoic acid or 2-ethylhexanoic acid.

The practice of the invention may be further appreciated by consideration of the following examples and comparative examples.

Ester base stocks 1 and 2 were prepared by reacting TMP for #1 and PE for #2 with pentanoic acid in the manner described in U.S. Pat. No. 5,021,179 column 8 lines 9–62, using sodium hydroxide to remove residual acidity in the manner generally known in the art as "alkali refining".

Different lots of each type of ester base stock were made at different times, using the same nominal directions but producing slightly different results, probably because of variations in the raw materials and/or process conditions within the ranges of permissible variation and practical control of these factors. The refined and dried ester lubricants were then treated according to the present invention with 0.5% of their mass of Alumina F-1 with a particle size of −100 mesh, commercially obtainable from Alcoa Industrial Chemicals Division (Vidalia, La.), for 1–2 hours per treatment step at 120° C. In some cases, as indicated in Table 1 below, more than one step of alkali refining and/or alumina treatment were used. The electrical resistance values were measured according to ASTM D 1169-80, using a test voltage of 500 volts per mm at a temperature of 25° C.

TABLE 1

| Ester Type and Lot No. | Number of Repetitions of: Alumina | Number of Repetitions of: Alkali | Acid Value | Tera-ohm. Cm |
|---|---|---|---|---|
| 1.1 | 1 | 1 | 0.004 | 1196 |
|  | 2 | 1 | 0.006 | 2286 |
|  | 4 | 1 | 0.006 | $232_0$ |
|  | 1 | 4 | 0.004 | $162_0$ |
|  | 4 | 4 | 0.004 | $238_0$ |
| 2.1 | 0 | 1 | 0.006 | 643 |
| 2.2 | 1 | 4 | 0.029 | $58_0$ |

It is apparent from the results in Table 1 that alumina treatment is more effective than alkali refining in increasing electrical volume resistivity.

The invention claimed is:

1. The process for increasing the electrical resistivity of a liquid mixture consisting essentially of esters of hindered polyols with organic carboxylic acids, which is used with chlorine-free hydrofluorocarbon refrigerants, said process comprising the steps of:

(1) pretreating the liquid mixture by alkali refining in order to reduce the acid value of the mixture;

(2) mixing the pretreated liquid mixture with solid activated alumina so as to form a solid-liquid mixture and maintaining mutual contact between the liquid and the alumina in said solid-liquid mixture at a temperature of at least 30° C. for a period of time;

(3) separating the solid material from the liquid in the solid-liquid mixture formed at the end of step (2) to produce a second liquid consisting essentially of esters of hindered polyols with organic carboxylic acids;

(4) mixing the second liquid mixture with solid activated alumina so as to form a solid-liquid mixture and maintaining mutual contact between the liquid and the alumina in said solid-liquid mixture at a temperature of at least 30° C. for a period of time; and (5) separating the solid material from the liquid in the solid-liquid mixture formed at the end of step (4) to produce a third liquid consisting essentially of esters of hindered polyols with organic carboxylic acids and having an electrical resistivity that is higher than that of the first liquid mixture.

2. The process according to claim 1 wherein the alkali refining step (1) is carried out with sodium hydroxide.

3. The process according to claim 1 wherein the mutual contact during each of steps (2) and (4) is carried out at a temperature of at least 72° C.

4. The process according to claim 3 wherein the mutual contact during each of steps (2) and (4) is carried out at a temperature of at least 119° C.

5. The process according to claim 1, wherein the contact time between solid-liquid mixture in each of steps (2) and (4) is not less than 1 minute.

6. The process according to claim 1 wherein the ratio of the mass of activated alumina to the mass of liquid treated in each of steps (2) and (4) is not less than 0.01%.

7. The process according to claims 6 wherein the ratio of the mass of activated alumina used to the mass of liquid treated in each of steps (2) and (4) is not less than 0.48%.

8. The process according to claim 1 wherein the average particle size of the activated alumina used in each of steps (2) and (4) is fine enough to pass through screens with standard mesh sizes of 24 but not fine enough to pass through screens with standard mesh size of 320.

9. The process according to claim 1 wherein the specific surface area of the alumina used in each of steps (2) and (4) is at least 100 m$^2$/g.

10. The process according to claim 1 wherein the mutual contact during each of steps (2) and (4) is carried out at least in part under reduced pressure.

11. The process according to claim 10 wherein said mutual contact in each of steps (2) and (4) is carried out at least in part at a pressure of not more than 10 torr.

12. The process according to claim 1 wherein the separated third liquid is subsequently dried.

13. The process according to claim 12 wherein the drying of said separated third liquid is effected by subjecting the third liquid to a temperature of about 120° C. for about 2 hours and under a reduced atmospheric pressure between 0.2 torr to about 2.0 torr.

14. A liquid mixture of esters of hindered polyols with organic carboxylic acids made from the process according to claim 1 wherein the esters have an electrical resistivity of at least $2.0 \times 10^{14}$ ohm-cm.

15. A process for increasing the electrical resistivity of a first liquid mixture consisting essentially of esters of hindered polyole with organic carboxylic acids, which is used with chlorine-free hydrofluorocarbon refrigerants, said process comprising the steps of:

(1) pretreating the first liquid mixture by alkali refining in order to reduce the acid value of the mixture;

(2) mixing the pretreated liquid mixture with solid activated alumina so as to form a solid-liquid mixture and maintaining mutual contact between the liquid and the alumina in said solid-liquid mixture at a temperature of at least 30° C. for a period of time;

(3) separating the solid material from the liquid in the solid-liquid mixture formed at the end of step (2) to produce a second liquid mixture consisting essentially of esters of hindered polyols with organic carboxylic acids;

(4) mixing the second liquid mixture with solid activated alumina so as to form a solid-liquid mixture and maintaining mutual contact between the liquid and the alumina in said solid-liquid mixture at a temperature of at least 30° C. for a period of time; and (5) separating the solid material from the liquid in the solid-liquid mixture formed at the end of step (4) to produce a third liquid mixture consisting essentially of esters of hindered polyols with organic carboxylic acids and having an electrical resistivity that is higher than that of the first liquid mixture wherein the esters of said first liquid mixture include:

(A) an ester made by reacting one or more of NPG, TMP, and PE with 2-ethylhexanoic acid;

(B) a mixture of polyol ester molecules in which (1) at least about 45% of the alcohol moieties are those of TMP and a total of at least about 75% of the remainder of the alcohol moieties are selected from those of the group consisting of NPG, TMP and PE and (2) at least 70% of the acyl groups are straight-chain pentanoyl groups and at least about 75% of the balance of the acyl groups are those selected from the group consisting of butanol, 2-methylpropanoyl, 2-methylbutanoyl, and 3-methylbutanoyl;

(C) a mixture of polyol ester molecules in which at least about 92% of the alcohol moieties are selected from the group consisting of the alcohol moieties derived from TMP, DTMP, PE and DPE and at least about 92% of the acyl groups are selected from the group consisting of the acyl groups of all the straight and branched chain monobasic and dibasic carboxylic acids with from four to twelve carbon atoms each, said alcohol moieties and acyl groups being further selected subject to the constraints that (a) a total of at least about 3% of the acyl groups in the mixture are acyl groups of i-$C_5$ acid; (b) the ratio of the % of acyl groups in the mixture that contain 8 or more carbon atoms and are unbranched to the % of acyl groups in the mixture that are both branched and contain not more than six carbon atoms is not greater than about 81; (c) not more than about 2% of the acyl groups in the ester mixture are part of acid molecules with more than two carboxyl groups each; and either (d) (1) a total of at least about 20% of the acid molecules in the mixture are one of the trimethylhexanoic acids at least about 90% of the alcohol moieties in the esters are those of PE; and not more than about 7.5% of the acyl groups in the ester mixture are dibasic; or (d) (2) at least about 2.0%, but not more than about 13%, of the acyl groups in the ester mixture are dibasic; and a total of at least about 82% of the monobasic acyl groups in the acid mixture have either five or six carbon atoms each;

(D) a mixture of polyol ester molecules in which at least about 92% of the alcohol moieties are selected form the group consisting of the alcohol moieties derived from TMP, DTMP, PE, DPE, TPE and TTMP and at least about 92% of the acyl groups are selected subject to the constraints that (a) a total of at least about 5% of the acyl groups in the mixture are acyl groups of i-$C_5$ acid; (b) the ratio of the % of acyl groups in the mixture that contain 8 or more carbon atoms and are unbranched to the % of acyl groups in the mixture that are both branched and contain not more than six carbon atoms is not greater than about 1.56; (c) the % of the acyl groups in the mixture that contain at least nine carbon atoms, whether branched or not, is not greater than about 81; and (d) not more than about 2% of the acyl groups in the ester mixture are part of acid molecules with more than two carboxyl groups each; and either (d) (1) a total of at least, about 20% of the acid molecules in the mixture are one of the trimethylhexanoic acids; at least about 90% of the alcohol moieties in the ester are those of PE; and not more than about 7.5% of the acyl groups in the ester mixture are dibasic; or (d) (2) at least about 5.5%, but not more than 13.5% of the acyl groups in the ester mixture are dibasic; and a total of at least about 82% of the monobasic acyl groups in the acid mixture have either five or six carbon atoms each;

(E) a mixture of polyol ester molecules in which at least about 92% of the alcohol moieties are selected from the group consisting of the alcohol moieties derived from TMP, DTMP, PE, DPE, TPE and TTMP and at least about 92% of the acyl groups are selected from the group consisting of the acyl groups of all the straight and branched chain monobasic and dibasic carboxylic acids with from four to twelve carbon atoms each, said alcohol moieties and acyl groups being further selected subject to the constraints that (a) a total of at least about 5% of the acyl group in the mixture are acyl groups of i-$C_5$ acid; (b) the ratio of the % of acyl groups in the mixture that contain 8 or more carbon atoms and are unbranched to the % of acyl groups in the mixture that are both branched and contain not more than six carbon atoms is not greater than about 1.56; (c) the % of acyl groups in the mixture that contain at least nine carbon atoms whether branched or not, is not greater than about 81; (d) not more than about 2% of the acyl groups in the ester mixture contain more than two carboxyl groups each ; and (e) at least about 13.8% of the acyl groups in the ester mixture are dibasic; and a total of at least about 82% of the monobasic acyl groups in the acid mixture have either five or six carbon atoms each; or (F) a mixture of polyol ester molecules in which at least about 85% of the alcohol moieties are selected from the group consisting of the alcohol moieties derived from PE, DPE and TPE, at least about 20% of the alcohol moieties are selected from the group consisting of the alcohol moieties derived from DPE and TPE, and at least about 92% of the acyl groups are selected from the group consisting of the acyl groups of all the straight and branched chain monobasic and dibasic carboxylic acids with from four to twelve carbon atoms each, said alcohol moieties and acyl groups being further selected subject to the constraints that (a) a total of at least about 3% of the acyl groups in the mixture are acyl groups of i-$C_5$ acid; (b) the ratio of the % of acyl groups in the mixture that contain 8 or more carbon atoms and are unbranched to the e of acyl groups in the mixture that are both branched and contain not more than six carbon atoms is not greater than 1.56; (c) the % of acyl groups in the mixture that contain at least nine carbon atoms, whether branched or not, is not greater than about 81; (d) not more than about 2% of the acyl groups in the ester mixture are part of acid molecules with more than two carboxyl groups each; and (e) a total of at least about 20% of the acyl groups in the mixture are selected from the group consisting of the trimethylhexanoyl acyl groups and not more than about 7.5% of the acyl groups in the ester mixture are dibasic.

16. The process according to claim 15 wherein the alkali refining step (1) is carried out with sodium hydroxide.

17. The process according to claim 15 wherein the mutual contact during each of steps (2) and (4) is carried out at a temperature of at least 72° C.

18. The process according to claim 17 wherein the mutual contact during each of the steps (2) and (4) is carried out at a temperature of at least 119° C.

19. The process according to claim 15 wherein the contact time between the solid-liquid mixture in each of steps (2) and (4), is not less than 1 minute.

20. The process according to claim 19 wherein the contact time between the solid-liquid mixture in each of steps (2) and (4) is not less than 56 minutes.

21. The process according to claim 15 wherein the ratio of the mass of activated alumina to the mass of liquid treated in each of steps (2) and (4) is not less than 0.01%.

22. The process according to claim 21 wherein the ratio of the mass of activated alumina used to the mass of liquid treated in each of steps (2) and (4) is not less than 0.48%.

23. The process according to claim 15 wherein the average particle size of the activated alumina used in each of steps (2) and (4) is fine enough to pass through screens with standard mesh sizes of 24 but not fine enough to pass through screens with standard mesh size of 320.

24. The process according to claim 15 wherein the specific surface area of the alumina used in each of steps (2) and (4) is at least 100 $m^2/g$.

25. The process according to claim 15 wherein the mutual contact in each of the steps (2) and (4) is carried out at least in part under reduced pressure.

26. The process according to the claim 25 wherein said mutual contact in each of step (2) and (4) is carried out at least in part at a pressure of not more than 10 torr.

27. The process according to claim 15 wherein the separated third liquid is subsequently dried.

28. The process according to claim 27 wherein the drying of said separated third liquid is effected by subjecting the third liquid to a temperature of about 120° C. for about 2 hours and under a reduced atmospheric pressure between 0.2 torr to about 2 torr.

29. A liquid mixture of esters of hindered polyols with organic carboxylic acid made from the process according to claim 15 wherein the esters have an electrical resistivity of at least $2.0 \times 10^{14}$ ohm-cm.

\* \* \* \* \*